(12) United States Patent
Pieters et al.

(10) Patent No.: US 10,729,862 B2
(45) Date of Patent: Aug. 4, 2020

(54) INHALER DEVICE

(71) Applicant: Cipla Europe NV, Antwerp (BE)

(72) Inventors: Frank Pieters, Antwerp (BE); Xerxes Rao, Mumbai (IN)

(73) Assignee: CIPLA (EU) LIMITED, Surrey (GB)

( * ) Notice: Subject to any disclaimer, the term of this patent is extended or adjusted under 35 U.S.C. 154(b) by 954 days.

(21) Appl. No.: 15/126,475

(22) PCT Filed: Mar. 24, 2015

(86) PCT No.: PCT/GB2015/050866
§ 371 (c)(1),
(2) Date: Sep. 15, 2016

(87) PCT Pub. No.: WO2015/150734
PCT Pub. Date: Oct. 8, 2015

(65) Prior Publication Data
US 2017/0095626 A1   Apr. 6, 2017

(30) Foreign Application Priority Data

Mar. 29, 2014 (IN) .......................... 1159/MUM/2014

(51) Int. Cl.
*A61M 15/00* (2006.01)
(52) U.S. Cl.
CPC ...... *A61M 15/0091* (2013.01); *A61M 15/009* (2013.01); *A61M 15/0025* (2014.02);
(Continued)
(58) Field of Classification Search
CPC .......... A61M 15/0091; A61M 15/0013; A61M 15/0093; A61M 15/0095; A61M 15/0096; A61M 15/0098; A61M 15/002
See application file for complete search history.

(56) References Cited

U.S. PATENT DOCUMENTS

| 4,972,830 A | 11/1990 | Wong et al. |
| 5,069,204 A | 12/1991 | Smith et al. |

(Continued)

FOREIGN PATENT DOCUMENTS

| IN | 1159MUM2014 | 3/2014 |
| WO | 2005007226 A1 | 1/2005 |

(Continued)

OTHER PUBLICATIONS

Foreign communication from the priority application—International Search Report and Written Opinion of PCT/GB2015/050866 dated Jul. 3, 2015, 12 pages.

(Continued)

*Primary Examiner* — Peter S Vasat
(74) *Attorney, Agent, or Firm* — Conley Rose, P.C.; Rodney B. Carroll

(57) ABSTRACT

A device (20) is disclosed for dispensing a fluid supplied from an external fluid source. The device comprises a transducer (32) adapted to receive a fluid from the fluid source, and a collapsible linkage and trip link (502) coupling the transducer and the fluid source. The linkage has a collapsible joint inhibiting discharge of the fluid source when in a locked orientation. The device (20) further comprises a moveable member coupled to the linkage such that inhalation forces on the device cause the linkage to collapse thereby discharging the fluid from the fluid source. The device may further include a dose counter coupled to the fluid source for registering the amount of doses administered from the fluid source.

14 Claims, 7 Drawing Sheets

(52) U.S. Cl.
CPC .... *A61M 15/0026* (2014.02); *A61M 15/0068* (2014.02); *A61M 15/0075* (2014.02); *A61M 15/007* (2014.02); *A61M 2205/585* (2013.01)

(56) References Cited

U.S. PATENT DOCUMENTS

| | | | | |
|---|---|---|---|---|
| 7,600,512 | B2 * | 10/2009 | Lee .................... | A61M 15/009 128/203.15 |
| 2005/0028812 | A1 * | 2/2005 | Djupesland ....... | A61M 15/0091 128/200.21 |
| 2006/0150971 | A1 * | 7/2006 | Lee ................... | A61M 15/0093 128/203.15 |

FOREIGN PATENT DOCUMENTS

| | | |
|---|---|---|
| WO | 2007066140 A1 | 6/2007 |
| WO | 2012150427 A1 | 11/2012 |
| WO | 2015150734 A1 | 10/2015 |

OTHER PUBLICATIONS

Foreign communication from a related counterpart application—Official Letter Examining Bangladesh Patent Application No. 85/2015/3205 dated Oct. 2, 2016, 1 page.

Foreign Communication from a related application—Examination Report of GCC Application No. GC 2015-29137, dated Jul. 12, 2018, 4 pages.

Foreign Communication from a related application—Official Action of European Application No. 15718076.1, dated Aug. 16, 2017, 5 pages.

Foreign communication from a related application—Office Action of Bolivian patent application No. 51-2015 dated Sep. 6, 2019, 4 pages.

Foreign communication from a related application—Examination report No. 2 of Australian Patent Application No. 2015242507, dated Jul. 19, 2019, 3 pages.

* cited by examiner

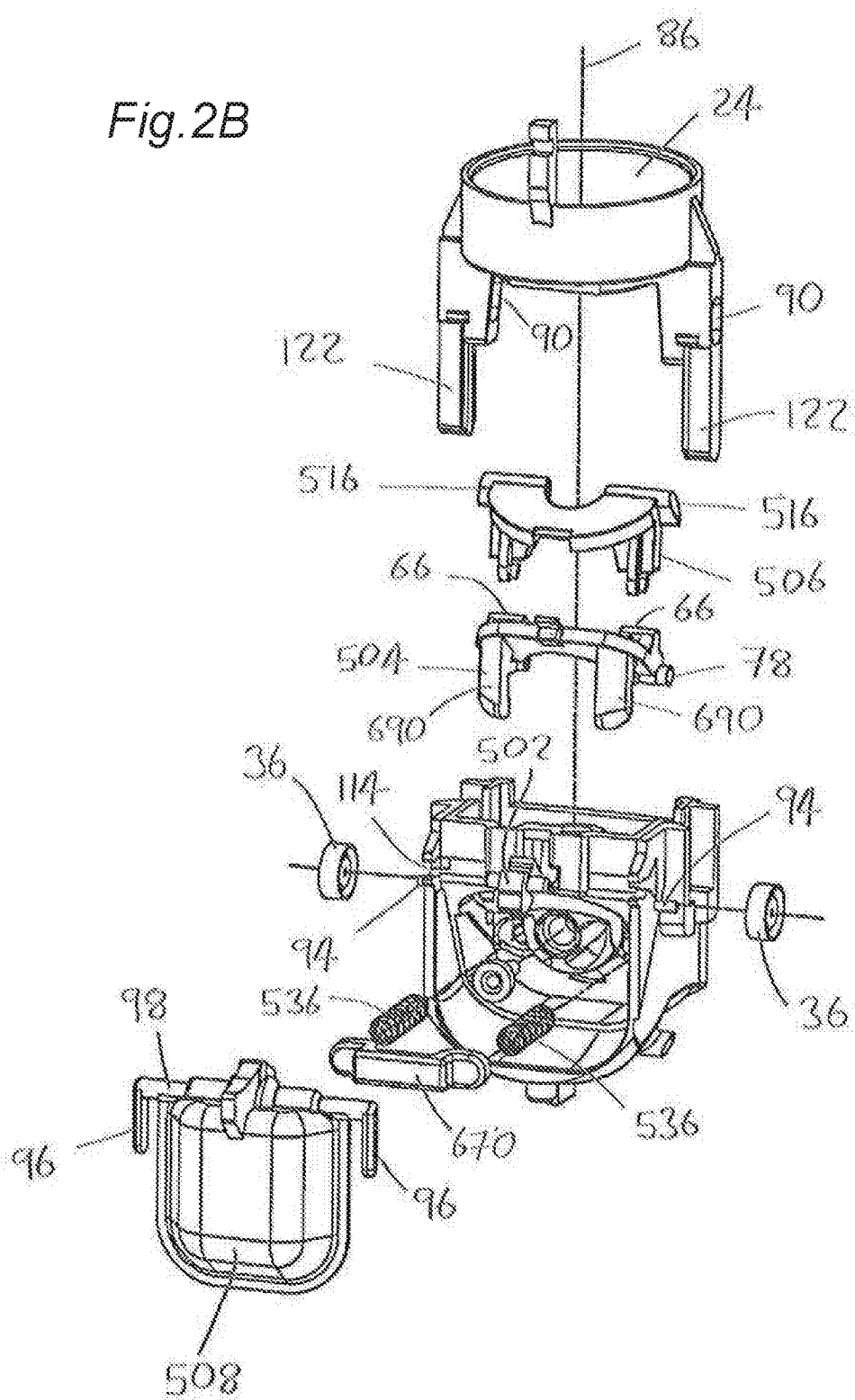

INHALER DEVICE

CROSS-REFERENCE TO RELATED APPLICATIONS

This application is a filing under 35 U.S.C. 371 of International Application No. PCT/GB2015/050866 filed Mar. 24, 2015, entitled "Inhaler Device," which claims priority to Indian Patent Application No. 1159/MUM/2014 filed Mar. 29, 2014, which applications are incorporated by reference herein in their entirety.

FIELD OF INVENTION

The present invention pertains generally to metered dose inhalers and, more specifically, to a metered dose inhaler with a breath actuated delivery mechanism and dose counter.

BACKGROUND OF THE INVENTION

Inhalers are commonly used to deliver a wide range of medicaments to the bronchial passages, lungs and bloodstream of the user. Typical inhalers hold a container of pressurized medicament and propellant that is actuatable, generally by compression, to deliver a dose of medicament through a mouthpiece to the patient.

It is generally desirable for the dose of medication to be dispensed at the same time that the patient inhales air to permit the majority of medication to enter the lung rather than the mouth or esophagus. A number of inhalers have been developed that use breath actuated devices to automatically initiate the discharge of the medicament from the container when the patient inhales. Many of these devices, such as U.S. Pat. No. 5,069,204 to Smith et al., use latching mechanisms that require a considerable amount of air pressure to release the medicament. These higher release pressures lead to difficulty of use, and discharge at non-optimal points in the patient's breath cycle.

The devices described in WO 2005/007226 and WO 2007/066140 are actuated with lower release pressures and are therefore more readily used by patients. However, the arrangements of these devices is such as to render assembly of the devices difficult and/or slow, particularly in relation to automated mass production.

It is therefore an object of the present invention to provide a breath-actuated inhaler device which is comparatively simple and/or quick to assemble.

SUMMARY OF THE INVENTION

A first aspect of the present invention provides an inhaler for dispensing metered doses of a medicament, the inhaler comprising a housing, an actuator member (508) moveable relative to the housing; a first link member (504) for coupling with a container of medicament; and a restraining surface (514) connectable with the first link member (504) for restraining movement of the first link member (504) from a first position, in which the medicament container is located in a stowed configuration, to a second position, in which the medicament container is located in a discharge configuration so as to dispense medicament; wherein the restraining surface (514) is moveable from a restraining position in response to movement of the actuator member (508) from a nominal position so as to allow movement of the first link member (504) from the first position to the second position; characterised in that the inhaler further comprises an elastically and resiliently deformable member (36) arranged adjacent the actuator member (508) so as to be compressed and thereby bias the actuator member (508) towards said nominal position.

Ideally, the deformable member (36) has an annular shape.

A circular hole defined by the annular shape of the deformable member (36) may receive a circular boss (94).

It is preferable that the diameter of the circular boss (94) is equal to or larger than the diameter of said hole defined by the annular shape of the deformable member (36) so that the boss (94) receives the deformable member (36) with an interference fit therebetween.

Furthermore, the boss (94) and deformable member (36) may be located adjacent a first side of the actuator member (508) and a second boss and second deformable member (36) may be located adjacent a second side of the actuator member (508) opposite said first side of the actuator member (508).

The actuator member (508) may comprise a projection (96) which extends therefrom so as to abut a deformable member (36).

It is preferable that the actuator member (508) comprises two projections (96), each projection (96) extending from a different opposite end of a hinge pin (98) and abutting a different deformable member (36).

The arrangement of projection (96) and deformable member (36) on a first side of the actuator member (508) relative to the opposite second side of the actuator member (508) may be asymmetric.

Ideally, said arrangement is asymmetric by virtue of two projections (96) located on either side of the actuator member (508) being arranged at an angle to one another.

A second aspect of the present invention provides an inhaler for dispensing metered doses of a medicament, the inhaler comprising a housing, an actuator member (508) moveable relative to the housing; a first link member (504) for coupling with a container of medicament; and a restraining surface (514) connectable with the first link member (504) for restraining movement of the first link member (504) from a first position, in which the medicament container is located in a stowed configuration, to a second position, in which the medicament container is located in a discharge configuration so as to dispense medicament; wherein the restraining surface (514) is moveable from a restraining position in response to movement of the actuator member (508) so as to allow movement of the first link member (504) from the first position to the second position; characterised in that the inhaler further comprises an elastically and resiliently deformable member (536) arranged adjacent the first link member (504) so as to be compressed and thereby bias the first link member (504) towards said first position.

Preferably, said deformable member (536) is a helical compression spring. It is also preferable for an end of said deformable member (536) to be retained in a desired position by virtue of said end being received by a boss (537).

The restraining surface (514) may be connectable with the first link member (504) by means of a trip link member (502) rotatably mounted to the housing.

The first link member (504) may be positioned relative to the trip link member so as to rotate the trip link member in a first rotary direction when moving from said first position to said second position; and the restraining surface (514) may be positioned relative to the trip link member, when in said restraining position, so as to restrain rotation of the trip link member in said first rotary direction.

It is preferable that the restraining surface (514) abuts a contact surface (512) of the trip link member when in said restraining position, and wherein the restraining and contact surfaces (514, 512) are arranged so as to slide relative to, and in abutment with, one another as the restraining surface is moved from the restraining position.

It is further preferable that the restraining surface is moveable from said restraining position along a part-circular path having a centre of curvature coincident with an axis about which the restraining surface is rotably mounted to the housing; and wherein said contact surface (512) has a part-cylindrical shape with a centre of curvature coincident with said axis of the restraining surface.

The restraining surface (514) may have a part-cylindrical shape with a center of curvature coincident with said axis about which the restraining surface is rotatably mounted. The first link member (504), when in said first position, is ideally located in a groove in the trip link member (502) and abuts a first side (510) of said groove.

The arrangement of the first link member (504) and the trip link member (502) may be such that the first link member (504), when in said second position, is spaced from the trip link member (502).

It is preferable that the first link member (504) is positioned relative to the trip link member so as to rotate the trip link member (502) when moving from said second position to said first position, the trip link member being rotated into a restrained position in which the restraining surface (514) is connectable therewith so as to restrain movement of the trip link member (502). The trip link member (502) may comprise a guide surface (524) for guiding the restraining surface (514) to the restraining position as the trip link member is rotated towards the restrained position.

Also, the guide surface (524) may cam the actuator member (508) as the trip link member (502) is rotated towards the restrained position. The restraining surface (514) is preferably provided on the actuator member (508). The actuator member (508) may be arranged so as to be moved, in use, in response to the inhalation of a user. Furthermore, the actuator member (508) is ideally a flap pivotally mounted to the housing.

Further aspects of the invention will be brought out in the following portions of the specification, wherein the detailed description is for the purpose of fully disclosing preferred embodiments of the invention without placing limitations thereon.

BRIEF DESCRIPTION OF THE DRAWINGS

Embodiments of the present invention will now be described with reference to the following drawings which are for illustrative purposes only and in which:

FIG. 2B is a second exploded view of the transducer of FIG. 2A, including a breath actuated release mechanism;

DETAILED DESCRIPTION OF THE INVENTION

Referring more specifically to the drawings, for illustrative purposes the present invention is embodied in the apparatus generally shown in FIGS. 1A, 1B, 2A and 2B, FIGS. 3A-D and FIG. 4. It will be appreciated that the apparatus may vary as to configuration and as to details of the parts, and that the method of operation may vary as to the specific steps and sequence, without departing from the basic concepts as disclosed herein.

Figure 1A:
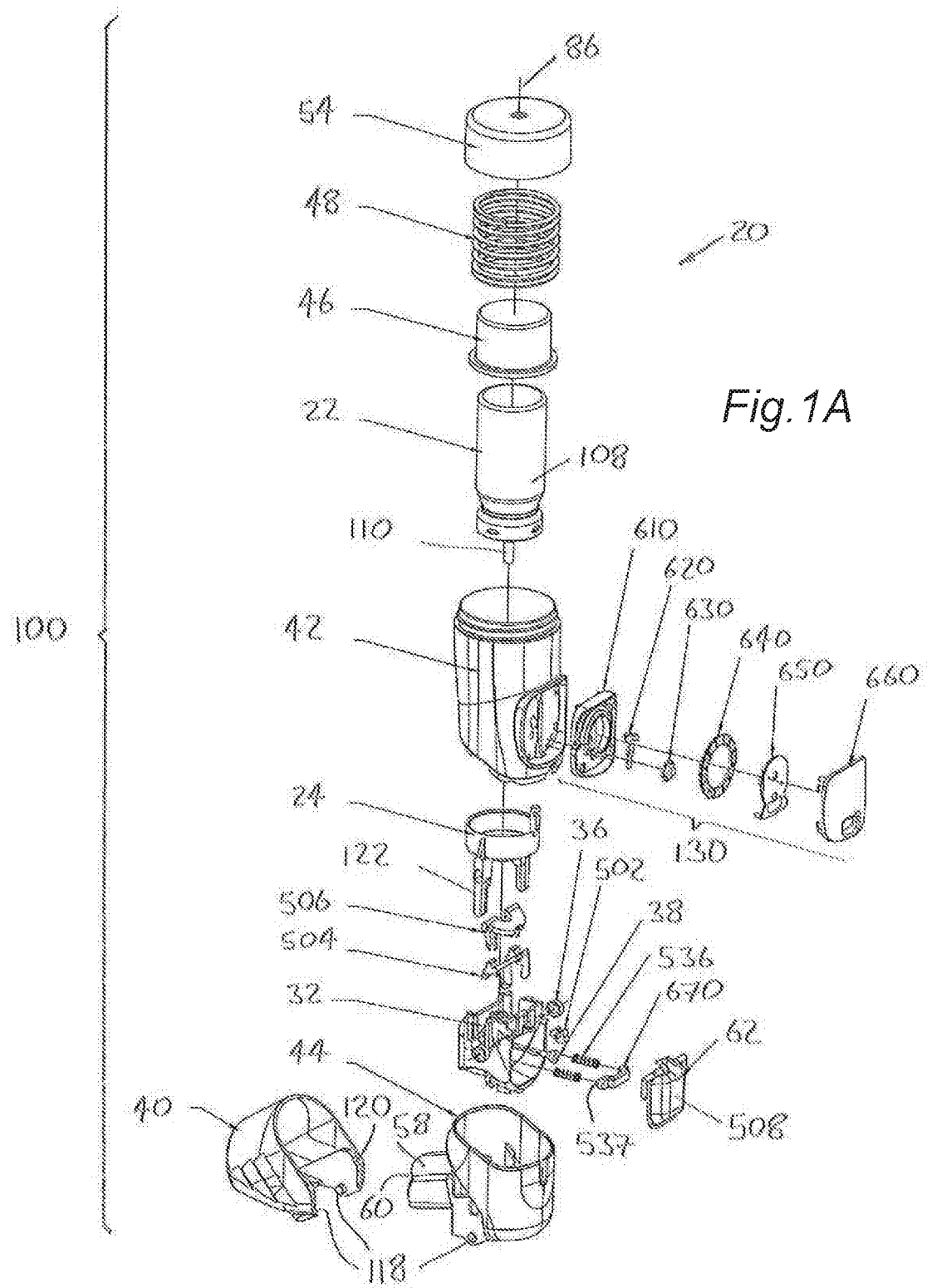
FIG. 1A is a first exploded view of an inhaler device according to the present invention, including a breath actuated release mechanism.
Figure 1B:
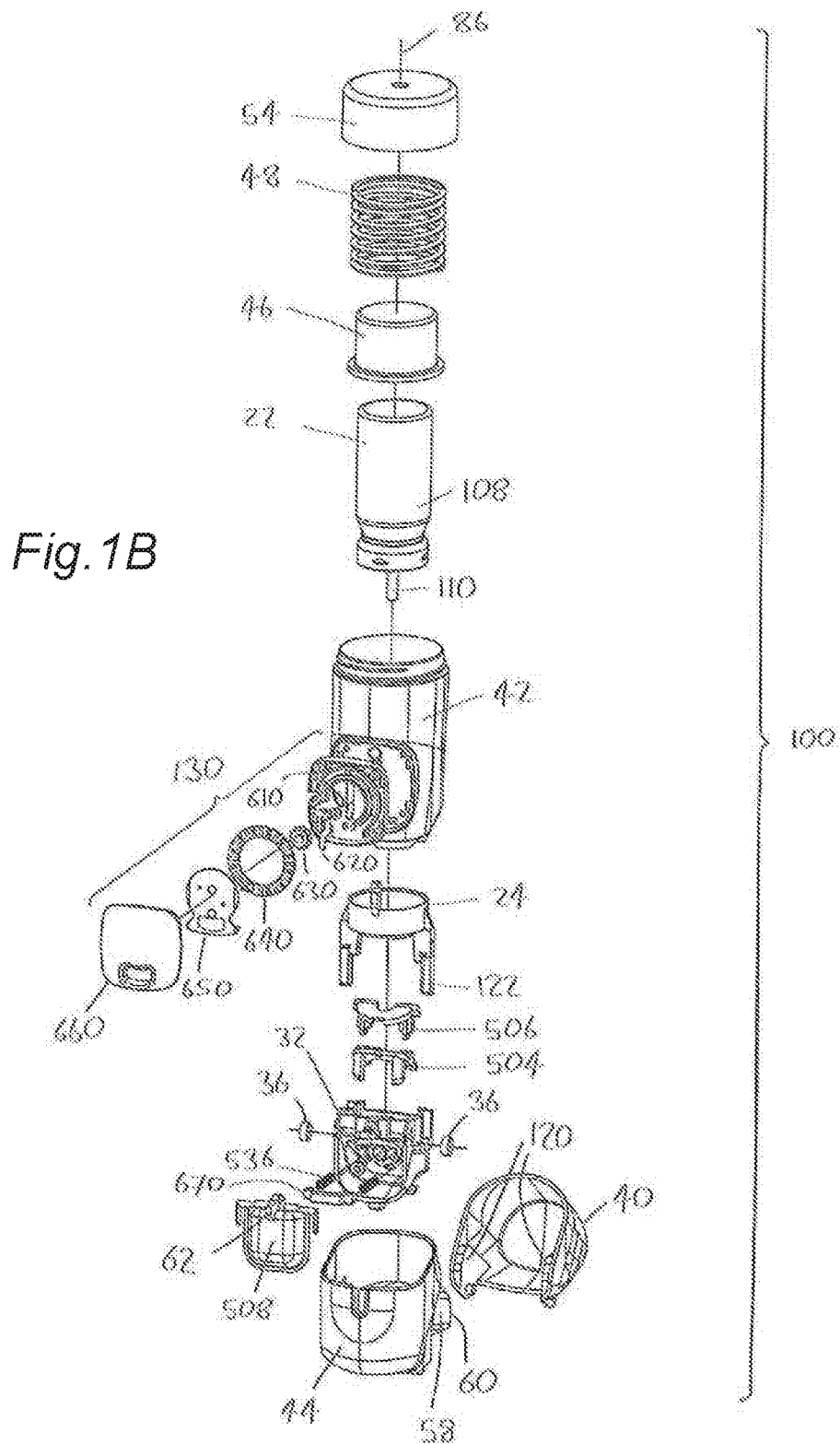
FIG. 1B is a second exploded view of the inhaler device of FIG. 1A, including a breath actuated release mechanism.

Referring first to FIGS. 1A and 1B, an inhaler 20 of the present invention is shown in an exploded view with a breath actuation assembly 100 and a dose counter assembly 130. The breath actuation assembly 100 and the dose counter assembly 130 are housed along with medicament fluid source 22 inside a main body 42, mouthpiece portion 44, and top cap 54, all preferably comprising medical grade plastic or other suitable materials known in the art. Once assembled, the main body 42 and mouthpiece portion 44 are ultrasonically welded to one another. The main body 42 and mouthpiece portion 44 are thereby secured to one another. It will be appreciated that the main body 42 and mouthpiece portion 44 may be secured to one another by other means, for example, such as by means of adhesive.

Fluid source 22 comprises a conventional Metered Dose Inhaler (MDI) container or other propellant based medicament readily available in the art. Fluid source 22 generally comprises a container 108 holding a mixture of medicament and propellant, and a nozzle 110, which is in line with a discharge axis 86 of the container 108, as shown in FIG. 1A. When the container 108 is advanced relative to the nozzle 110 in the direction of the discharge axis 86 (i.e. the nozzle 110 is pushed into the container 108), the medicament is discharged out the nozzle 110 in the direction of the discharge axis 86.

The inhaler 20 further includes a dust cover 40 pivotally mounted to cover an inhalation horn 58. The dust cover 40 may be rotated away from horn 58 to expose an opening 60. A manual release button 62 is also provided so as to extend through an aperture in the mouthpiece portion 44.

Referring also to FIGS. 1, 2 and 3, the breath actuation assembly 100 comprises a housing or transducer 32 that rotatably houses lower link 504 at pivot 78. Lower link 504 is connected to upper link 506 at collapsible joint 66. Container holder 24 is shaped to receive the nozzle end of container 108 such that the nozzle 110 passes through to contact surface 112 of the transducer 32. Container holder 24 also has a pair of guides 122 having slots 90 sized to house a pair of bosses 516 as shown in FIG. 2 at the upper end of upper link 506.

Figure 2A:
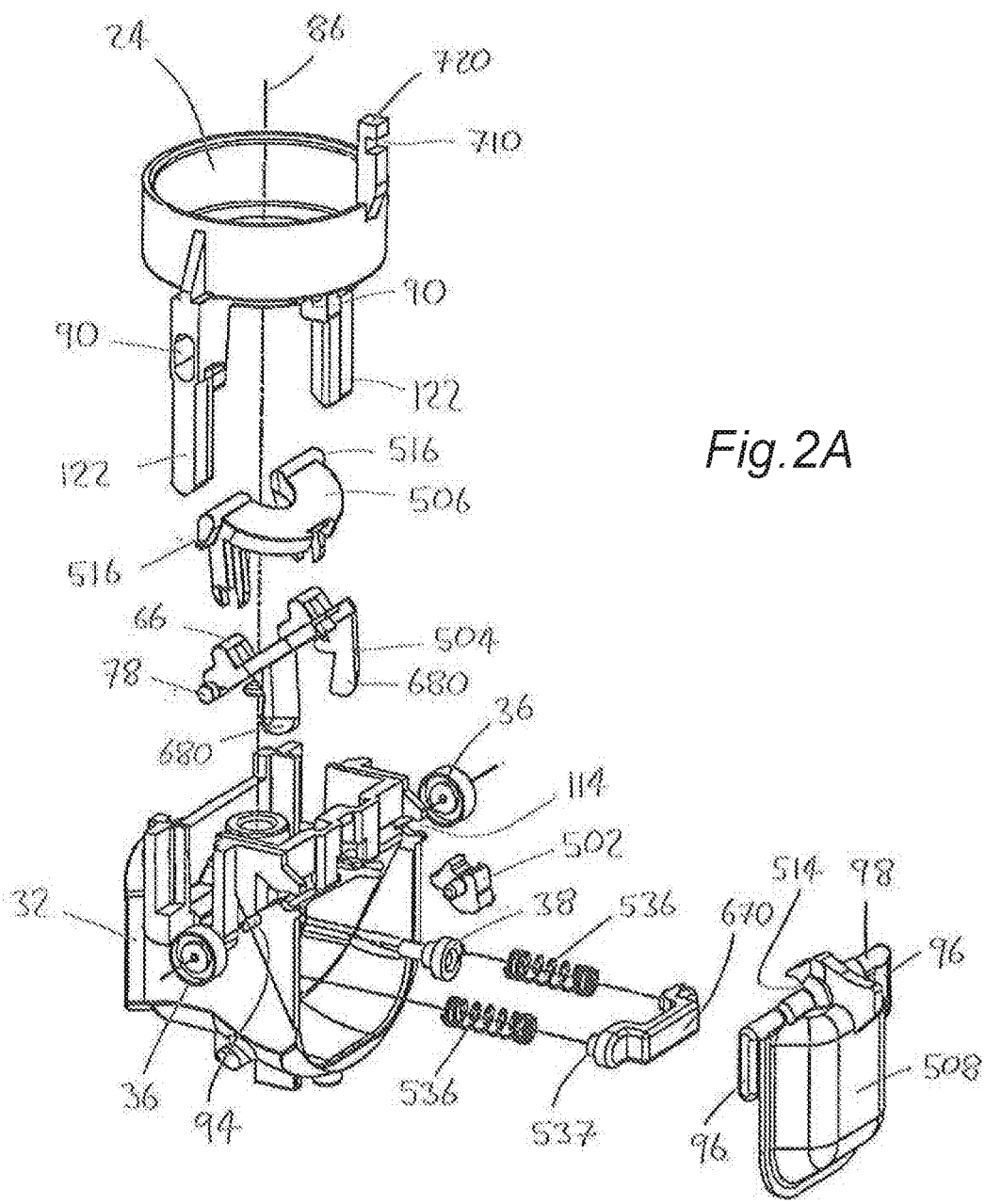
FIG. 2A is a first exploded view of a transducer of the inhaler device shown in FIG. 1, including a breath actuated release mechanism.

As shown in FIGS. 2A and 2B in particular, flap 508 is rotatably mounted to the transducer 32 via a peg 98, which extends across the top surface of flap 508, and holes 114 in the sidewalls of transducer 32. The holes 114 may be provided as slots into which the peg 98 is snap fitted during assembly of the apparatus. This allows ready assembly of the flap 508 to the transducer 32 by simply pressing the peg 98 of the flap 508 into the slots 114. Due to the snap fit nature of the peg 98 in the slots 114, the flap 508 is retained in a connection with the transducer 32 which allows rotation of the flap 508 relative to the transducer 32. The bottom and side extremities of flap 508 are sized to fit within the internal surface of transducer 32 to form gap between the flap 508 and said internal surface. The flap 508 has an upper restraining surface 514 configured, in combination with a trip link 502, to retain an arm of lower link 504 when the flap is in its nominal position shown in FIG. 3A.

Figure 4:
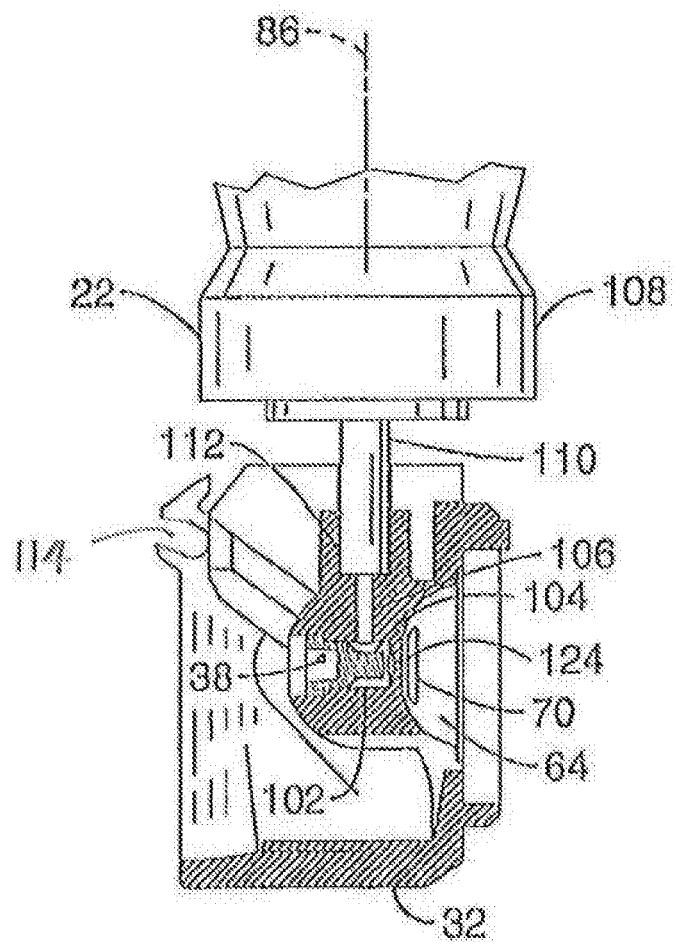
FIG. 4. is a cross-sectional schematic view the transducer of FIG. 2A with the fluid source in a stowed configuration.

As illustrated in FIG. 4, the transducer 32 is configured to receive nozzle 110 of fluid source 22 at surface 112. The transducer also comprises an inlet 106 that spans from surface 112 to a first chamber 102. The inlet 106 is configured to be in line with the nozzle 110 and discharge axis 86 such that medicament discharged from the fluid source 22 is received through the inlet 106 and downstream into first chamber 102.

The transducer 32 is also configured to receive plug 38 having bluff surface 104. Fluid entering chamber 102 through inlet 106 is dispersed and redirected by plug 38 and into outlet 124 that terminates downstream at a second chamber 64.

The fluid source 22 is biased to discharge along axis 86 by compressing a loading member, such as biasing spring 48, between the top cap 54 and container sleeve 46, which is adapted to receive the other end of the container 108 opposite the nozzle 110. Biasing spring 48 preloads the container 108 to move in the direction of surface 112 of transducer 32 along the discharge axis 86.

Figure 3A:
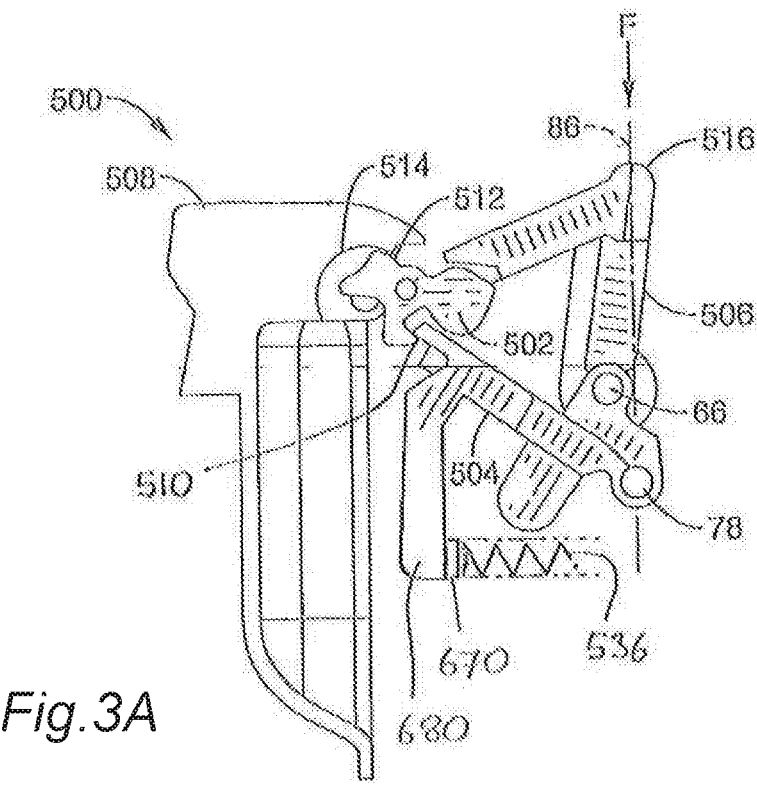
FIG. 3A-D is a schematic view illustrating motion of the breath actuated mechanism.

In the stowed configuration shown in FIG. 3A, the fluid source container 108 is retained from translating along axis 86 by a collapsible linkage comprising upper link 506 and lower link 504. Upper link 506 and lower link 504 are rotatably coupled at a collapsible knee-type joint 66. The upper end of upper link 506 has a pair of bosses 516 that are retained by a pair of guides 122 in the container holder 24 having slots 90. The guides are generally in-line, or at least parallel, with the discharge axis 86, and allow motion of the bosses 516 of the upper link to slideably translate upward and downward in the discharge axis 86, as well as allow the boss to rotate as necessary. The lower link 504 has one end fixed to the transducer 32 at pivot 78. As illustrated in FIG. 3A, the boss 516 of the upper link 506 and pivot 78 of the lower link are essentially in-line with discharge axis 86, i.e. they form a loading path that is parallel to, or aligned with, the discharge axis 86. Because collapsible joint 66 is off-center, i.e. positioned away from the loading path formed by the boss 516 of the upper link 506 and pivot 78, the downward force imposed by biasing spring 48 on the container 108 in the stowed position predisposes the knee joint 66 to collapse. Such collapse is restrained in the stowed position by imposition of the lower link 504 on the trip link 502 and, in turn, by imposition of the trip link 502 on the flap 508.

Figure 3B:
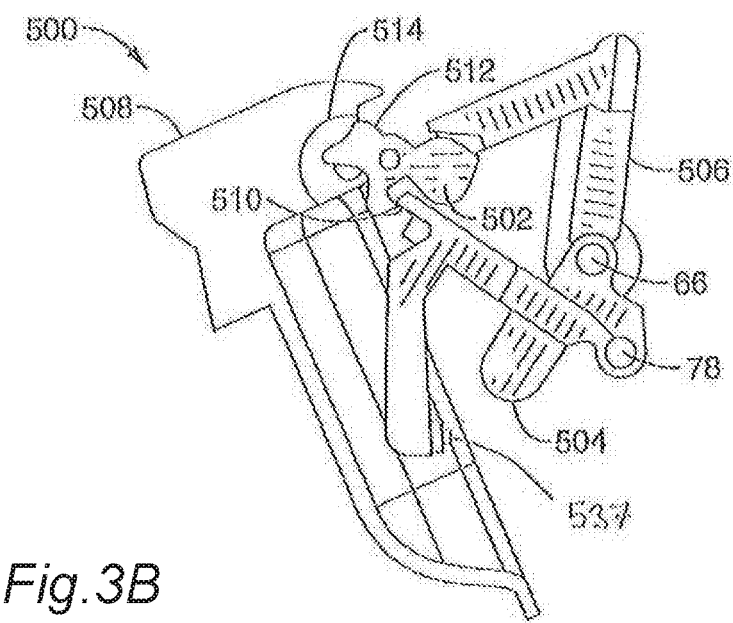
Figure 3C:
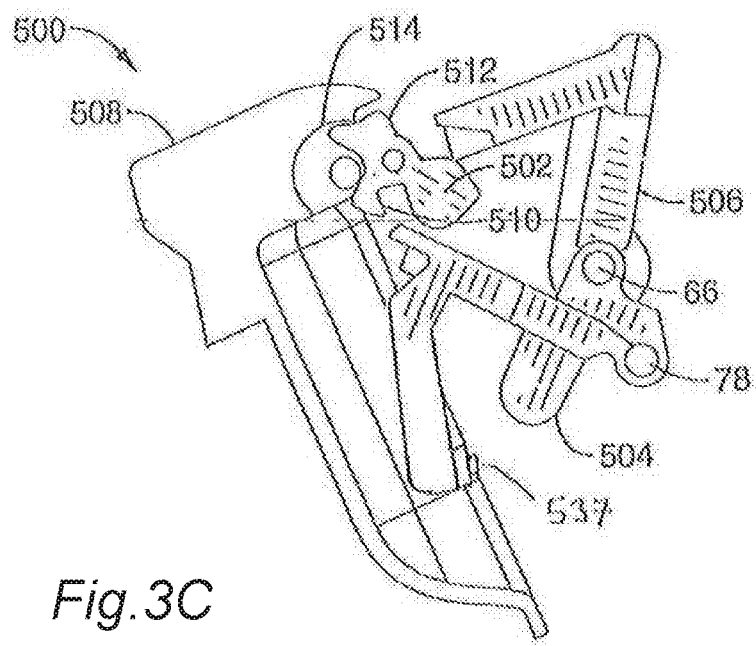
Figure 3D:
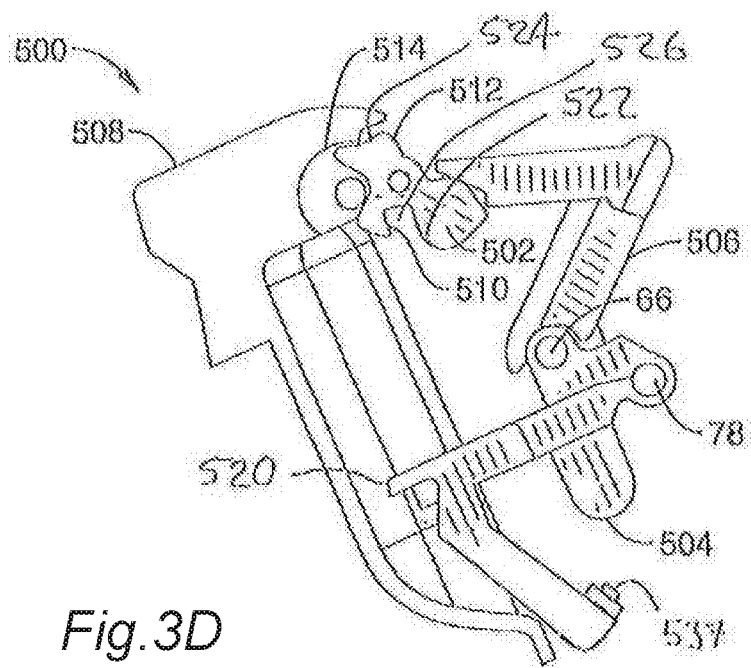

FIG. 3B illustrates the initiation of the breath actuation mechanism 100 caused by inhalation by a patient through the opening 60 of horn 58. An outward airflow is created in the second chamber 64, which pulls through a plurality of slots 70 in the transducer (see FIG. 4). Suction of air through slots 70 creates a small pressure differential across the inner surface of flap 508, causing the flap to rotate about peg 98 and into the cavity of the transducer 32, as illustrated in FIGS. 3B-3D. The gap between the flap 508 and the transducer 32 provides enough clearance to allow the flap to rotate into the cavity of the transducer, while also being small enough to allow a pressure differential with minimal suction on the horn. As the flap 508 rotates, the lower link 504 is no longer retained by the upper surface 514 of the flap, and the lower link 504 clears the flap 508 as the lower link 504 is allowed to rotate about pivot 78.

The breath actuation of the inhaler device, through use of breath actuation linkage 500 including the trip link 502 arrangement, will now be described in greater detail. In this regard, FIG. 3A illustrates the breath actuation mechanism in a ready (non-actuated, and loaded) state. It will be noted that rather than interfacing directly with flap 508, the lower link 504 interfaces indirectly with flap 508 via the trip link 502. The upper link 506 and lower link 504 retain motion of the fluid source 22 and load F from biasing spring via locking knee joint 66. Knee joint 66 is located off-center from the load F in discharge axis 86 (i.e. the discharge axis 86 passes through pivot 78 and the boss 516 of upper link 506 throughout FIGS. 3A-D), and thus the downward force imposed by biasing spring 48 on the container 108 in the ready state/position predisposes the knee joint 66 to collapse.

The upper link 506 and lower link 504 are restrained from rotating or collapsing because the lower link 504 is locked from rotation by a catch, or trip edge 510 in trip link 502. Trip link 502 is locked from rotating because of impingement of upper surface (contact surface) 512 of the trip link 502 with a restraining surface, or circular cutout 514, in the flap 508.

Referring now to FIG. 3B, when the flap 508 rotates due to the force created by patient inhalation (vacuum), upper edge 512 of the trip link clears the cutout 514, allowing the trip link 502 to rotate clockwise (as viewed in FIG. 3). Trip edge 510 correspondingly rotates to release the contacting surface of the lower link 504

With lower link 504 now unrestrained, as shown in FIG. 3C, knee joint 66 collapses and shifts to the left. Because of constraints on the top edges of upper link 506 with container holder 24, the upper link can only travel in line with the force load path F, and the trip link 502 further rotates clockwise (as viewed in FIG. 3), causing the lower link 504 to further rotate counter-clockwise (as viewed in FIG. 3).

Referring now to FIG. 3D, the mechanism further collapses as the lower link 504 continues to rotate counter-clockwise on joint 78, and upper link 506 travels down allowing the MDI canister 22 to travel downward causing the valve stem to activate.

After activation, the canister travels upwards such that the knee joint moves back towards its stowed orientation with lower link 504 rotating clockwise towards trip link 502. The trip link 502 is able to catch lower link 504 in trip edge 510 for retention of the knee joint 66 until subsequent breath actuation of flap 508.

The knee joint is moved back towards its stowed orientation by two return compression springs 536 (each in the form of a helical compression spring) which are elastically and resiliently compressed, and also elastically and resiliently bent, between the lower link 504 and transducer 32 when the linkage moves towards the collapsed configuration. The compression springs thereby tend to bias (i.e. return) the linkage into the locked position.

One compression spring 536 is shown (schematically represented) in FIG. 3A only. For the purposes of clarity, no return springs 536 are shown in FIGS. 3B-D.

Each compression spring 536 has a first end abutting the lower link 504 and a second end, opposite the first end, abutting an internal surface of the transducer 32. Bosses 537 may be provided projecting from the lower link 504 and the internal surface of the transducer 32, and located within the circular ends of the compression springs 536. The two bosses 537 (one for each spring 536) projecting from the lower link 504 are provided on either end of a single unitary member 670. This member 670 clips (or is otherwise secured, for example, by means of adhesive) to the lower link 504. For example, the member 670 may resiliently and elastically snap fit between free end portions 680 of two elongate elements 690 of the lower link 504 (see FIGS. 2A, 2B and 3A). Accordingly, each end of each compression spring is located about a boss 537 and is thereby retained in position by the respective boss 537 adjacent the lower link 504 or internal surface of the transducer 32. In the accompanying drawings, only one boss 537 is shown (which extends from the lower link 504 of the schematic arrangement of FIG. 3).

The flap 508 is returned to its nominal position in the same way as for the embodiment of FIG. 1.

The use of the trip link 502 assists in expanding the operational margin of the lower link 504 with the flap 508, improving overlap on trip edges to ease manufacturing tolerances while maintaining breath actuation sensitivity.

In particular, the addition of the trip link 502 expands the operational margin of the lower link 504 with the flap 508 in that, when in the ready state, the inhaler is less prone to accidental actuation as a result of a sudden movement or vibration of the inhaler which causes an unintended rotation of the flap 508. With reference to FIG. 3A, it will be seen that the amount of overlap between the cutout surface 514 and the meeting upper edge 512 is sufficient for the flap 508 be able to rotate a considerable distance without the trip link 502 being released so as to allow the knee joint 66 to collapse. Since the mating surfaces 514, 512 have a cylindrical shape with a concentric curvature, the area of contact between the flap 508 and trip link 502 remains comparatively large until just before the trip link 502 is released. This also contributes to rendering it more difficult to accidentally actuate the inhaler.

Furthermore, after actuation, the canister travels upward and the lower link 504 engages the trip link 502. An end 520 of the lower link 504 engages a portion 522 of the trip link 502 and pushes the trip link 502 so as to rotate said link 502 in an anti-clockwise direction (FIG. 3D). As the trip link 502 so rotates, the flap 508 may be cammed along a surface 524 of the trip link 502. The surface 524 is configured relative to the rotational axis of the trip link 502 so as to engage with the flap 508 in such a way that rotation of the trip link 502 is not prevented by the engagement therewith of the flap 508. The arrangement of the trip link surface 524 may be such that said surface is cylindrical with a center of curvature coincident with the rotational axis of the trip link 502. In this way, as the trip link 502 rotates in an anti-clockwise direction (as viewed in FIG. 3), the engagement between the flap 508 and trip link surface 524 is such that the flap 508 is not itself rotated. However, the surface 524 may be arranged so that, as the trip link 502 rotates in an anti-clockwise direction, the surface 524 allows a camming of the flap 508 back towards a ready state position. It will be understood therefore that the surface 524 facilitates a return of the linkage and flap 508 back to the ready state position and ensures a movement of the linkage back to this position is not prevented by the flap 508. In the schematic arrangement shown in FIG. 3, the surface 524 is arranged on the trip link 502 adjacent the upper edge 512.

As the lower link 504 pushes the trip link 502 in the anti-clockwise direction, the end 520 of the lower link 504 cams into a groove 526 partly defined by trip edge 510.

With rotation of the lower link 504 as shown in FIG. 3C, the collapsible joint 66 moves over center (i.e. the joint 66 moves yet further away from the loading path formed by the boss 516 of the upper link 506 and pivot 78), allowing the container holder 24 and container 108 to translate downward along axis 86, forcing a portion of the nozzle 110 into the container 108 to stimulate discharge of the medicament from the container 108. The medicament travels through the first chamber 102 and into the second chamber 64 where it is entrained with air flowing through slots 70, as described in further detail in U.S. Pat. No. 4,972,830, incorporated by reference. In the embodiment shown, the second chamber 64 has an internal cross section that is shaped like a parabola. The entrained medicament flows through the second chamber 64 and out of the opening 60 of horn 58 to be inhaled by the patient. Therefore, the release of the metered dose of medicament is timed to be inhaled by the patient at an optimal moment during the inhalation phase of the patient's breath cycle.

After the inhalation of the dose by the patient, the flap is returned to its nominal position shown in FIG. 3D by a return force exerted by flap springs 36. Rotation of the flap compresses each spring to create a return force to return the flap 508 to its nominal position after the inhalation forces have subsided.

The flap springs 36 are elastically and resiliently deformable members mounted to the exterior of opposite sides of the transducer 32. Each flap spring 36 may be manufactured from silicon or similar material known to a person skilled in the art. Furthermore, each spring 36 may be provided in the form of a pad. More specifically, each flap spring 36 has an annular/ring shape and the circular hole formed by this shape receives a circular boss 94 extending from each of said opposite side of the transducer 32. The diameter of each circular boss 94 is equal to or ideally larger than the diameter of said hole in flap spring 36 associated with said boss 94 so that an interference fit is provided between the boss 94 and flap spring 36 when the flap spring 36 is pressed onto the boss 94 during assembly. The flap spring 36 is thereby retained on the boss 94 (see FIGS. 2A and 2B in particular). It will be understood that pressing a flap spring 36 on to one of the bosses 94 is a simple process step allowing a ready and reliable assembly of the apparatus. Each flap spring 36 may be provided as a rubber washer or an O-ring.

The flap 508 is provided with two projections 96 (see FIGS. 1A to 2B) which extend from the peg 98. Specifically, each projection 96 extends from a different opposite end of the peg 98. Furthermore, each projection 96 extends so as to be parallel with the plane in which the flap 508 lies. The flap 508, peg 98 and projections 96 are fixed relative to one another such that, as the flap 508 rotates (permitted by rotation of the peg 98 in the holes or slots 114), the projections 96 also rotate. In the assembled apparatus, each projection is located to the exterior of said opposite sides of the transducer 32, and relative to the flap spring 36 and associated boss 94, so that the flap springs 36 abut the projections 96 when the flap 508 is in its nominal. As the flap 508 rotates from the nominal position, the projections 96 rotate and compress (i.e. flatten or reduce in dimension, rather than bend or twist as in the case of a leaf spring or torsion spring respectively) one circumferential section of the flap springs 36 with which they abut. As the flap 508 increasingly rotates, the flap springs 36 are increasingly compressed in an elastic and resilient fashion. The flap 508 is thereby biased towards its nominal position by means of the flap springs 36 pressing back against the projections 96.

It will be understood that the return force applied to the flap 508 may be adjusted in different embodiments by changing the material from which the flap springs 36 are made and/or by changing the size of the flap springs 36. The return force may also be adjusted by adopting an asymmetric arrangement of the flap springs 36 and projections 96 such that the arrangement of spring/projection on one side of the transducer 32 is different to that on the other side of the transducer 32. For example, the material and/or size of the spring 36 on one side of the transducer 32 may be different to that on the other side. The relative position of the spring 36 and projection 96 on one side of the transducer 32 may be different to that on the other side. This may, for example, result in an initial movement of the flap 508 from its nominal position to a second position causing compression of only one flap spring 36, with the second flap spring 36 being abutted and compressed by the second projection 96 only with rotation of the flap 508 continuing from said second position of flap 508. This arrangement could take the form of the two projections 96 being arranged at an angle to one another rather than parallel to one another as shown in the accompanying drawings.

In an alternative embodiment, each flap spring could be an elastically and resiliently deformable member in the shape of a solid or hollow cylinder. Such a deformable member may extend from a side of the transducer 32. The deformable member could be secured adjacent the side of the transducer 32 by one of numerous means, for example, by means of an adhesive, or alternatively the side of the transducer 32 could be provided with a hole in which the deformable member is held.

The upper and lower links 506, 504, container holder 24, and container 108 remain in the collapsed discharge position as seen in FIG. 3D due to the force imposed by the biasing spring 48. The return of the dust cover 40 to cover the horn 58 manually forces the container holder 24 and container 108 to return to the stowed position under compression from biasing spring 48. As mentioned above, the links 504,506 are biased towards the position shown in FIG. 3A by a compression spring (for example, a helical compression spring) which is increasingly elastically and resiliently compressed (and perhaps also elastically and resiliently bent) between the lower link 504 and transducer 32 when the linkage moves towards the collapsed configuration shown in FIG. 3D. The compression spring thereby tends to bias the linkage into the locked position. The collapsible joint 66 is thus retained from collapsing once the dust cover 40 is again opened. The operation of the dust cover 40 will now be described. In the present embodiment, the dust cover 40 not only serves as a shield to cover horn opening/entrance 60, but it also serves to reset the container to the stowed position after discharge of the medicament. In the stowed position/configuration, the inhaler 20 is arranged with the dust cover 40 shielding the entrance 60 to horn 58 and the links 504,506 positioned as shown in FIG. 3A. The dust cover 40 is pivotably connected to the transducer 32 such that it can be rotated out of place to allow access to the horn opening 60. The dust cover 40 has two cams 120 (see FIG. 1A), which are configured to engage the bottom surface of the guides 122 of the container holder 24 through its entire range of motion along axis 86. When the dust cover 40 is rotated about a pivot arrangement 118 (shown in FIG. 1A) so as to open the entrance 60 to the horn 58, the cams disengage with the guides 122. The container holder 24 and container 108 remain in the stowed position, as shown in FIG. 3A, because of the orientation of the collapsible linkage being retained by the rotational locking of the lower link 504 by the trip edge 510 in trip link 502.

FIG. 3D illustrates the breath actuation assembly 100 in the collapsed configuration with the container holder 24 and container 108 in the discharge position. The breath actuation assembly 100 is biased to remain in this configuration due to the compressive force of the biasing spring 48. When the dust cover is rotated back toward the horn opening 60, the cams 120 (see FIG. 1) provided on the dust cover 40 engage the bottom surface of guide 122, pushing the container holder 24 and container 108 upward along axis 86. When the dust cover 40 is in its final stowed position covering the horn opening/entrance 60, the cams 120 have pushed the container holder 24 to the stowed position. In this configuration, the return springs 536 have reset the breath actuation assembly 100 to the locked position, and movement of the container 108 will be retained by the dust cover cams independent of the collapsible linkage.

The inhaler preferably includes a dose counter for automatically counting the remaining doses left in the container after each discharge of the medicament. The inhaler may be configured with a dose counter having a number of different configurations, including mechanical or electrical counters. The inhaler 20 shown in the accompanying drawings has a dose counter assembly 130 located in a rear side of the main body 42. The dose counter assembly 130 includes a dose counter casing 610, an activation lever 620, a drive gear 630, a dose counter indicator 640, a lens 650, and a dose counter cover 660. The dose counter assembly 130 may be constructed following the teachings of WO 2012/150427, the disclosure of which is incorporated herein by reference. The activation lever 620 engages in a slot 710 provided in a projection 720 extending upwardly from the container holder 24 (see FIG. 2A).

It will however be understood that an alternative arrangement of dose counter may be used, for example such as that referred to in WO 2005/007226 or WO 2007/066140. Alternatively, the dose counter assembly 130 may be omitted and an inhaler provided without a dose counter assembly.

The present invention is not limited to the particular embodiments described above and alternative arrangements and suitable materials will be apparent to a reader skilled in the art. Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more". All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims.

The invention claimed is:

1. An inhaler for dispensing metered doses of a medicament, the inhaler comprising a housing, an actuator member (508) moveable relative to the housing; a first link member (504) for coupling with a medicament container; and a restraining surface (514) connectable with the first link member (504) for restraining movement of the first link member (504) from a first position, in which the medicament container is located in a stowed configuration, to a second position, in which the medicament container is located in a discharge configuration so as to dispense medicament; wherein the restraining surface (514) is moveable from a restraining position in response to movement of the actuator member (508) so as to allow movement of the first link member (504) from the first position to the second position;

characterised in that the inhaler further comprises an elastically and resiliently deformable member (536) arranged adjacent the first link member (504) so as to be compressed as the first link member moves towards the second position and thereby bias the first link member (504) towards said first position, wherein said elastically and resiliently deformable member (536) is a helical compression spring, wherein an end of said elastically and resiliently deformable member (536) is retained in a desired position by virtue of said end receiving a boss (537) and in which there are two helical compression springs (536) and each has a first end abutting the first link member (504) and a second end abutting an internal surface of the housing, the first link member including bosses (537) projecting therefrom which are located within ends of the compression springs (536), the bosses (537) being provided on a member (670), the member (670) being secured between free end portions (680) of elongate elements (690) of the lower link (504).

2. The inhaler as claimed in claim 1, wherein the restraining surface (514) is connectable with the first link member (504) by means of a trip link member (502) rotatably mounted to the housing.

3. The inhaler as claimed in claim 2, wherein the first link member (504) is positioned relative to the trip link member so as to rotate the trip link member in a first rotary direction when moving from said first position to said second position; and the restraining surface (514) is positioned relative to the trip link member, when in said restraining position, so as to restrain rotation of the trip link member in said first rotary direction.

4. The inhaler as claimed in claim 3, wherein the restraining surface (514) abuts a contact surface (512) of the trip link member when in said restraining position, and wherein the restraining and contact surfaces (514, 512) are arranged so as to slide relative to, and in abutment with, one another as the restraining surface is moved from the restraining position.

5. The inhaler as claimed in claim 4, wherein the restraining surface is moveable from said restraining position along a part-circular path having a centre of curvature coincident with an axis about which the restraining surface is rotably mounted to the housing; and wherein said contact surface (512) has a part-cylindrical shape with a centre of curvature coincident with said axis of the restraining surface.

6. The inhaler as claimed in claim 5, wherein the restraining surface (514) has a part-cylindrical shape with a centre of curvature coincident with said axis about which the restraining surface is rotably mounted.

7. The inhaler as claimed in claim 2, wherein the first link member (504), when in said first position, is located in a groove in the trip link member (502) and abuts a first side (510) of said groove.

8. The inhaler as claimed in claim 7, wherein the arrangement of the first link member (504) and the trip link member (502) is such that the first link member (504), when in said second position, is spaced from the trip link member (502).

9. The inhaler as claimed in claim 2, wherein the first link member (504) is positioned relative to the trip link member so as to rotate the trip link member (502) when moving from said second position to said first position, the trip link member being rotated into a restrained position in which the restraining surface (514) is connectable with the trip link member so as to restrain movement of the trip link member (502).

10. The inhaler as claimed in claim 9, wherein the trip link member (502) comprises a guide surface (524) for guiding the restraining surface (514) to the restraining position as the trip link member is rotated towards the restrained position.

11. The inhaler as claimed in claim 10, wherein the guide surface (524) cams the actuator member (508) as the trip link member (502) is rotated towards the restrained position.

12. The inhaler as claimed in claim 2, wherein the restraining surface (514) is provided on the actuator member (508).

13. The inhaler as claimed in claim 2, wherein the actuator member (508) is arranged so as to be moved, in use, in response to the inhalation of a user.

14. The inhaler as claimed in claim 2, wherein the actuator member (508) is a flap pivotally mounted to the housing.

* * * * *